(12) United States Patent
Bare et al.

(10) Patent No.: US 11,737,798 B2
(45) Date of Patent: *Aug. 29, 2023

(54) SURGICAL SCREW SYSTEM

(71) Applicant: ARTHREX, INC., Naples, FL (US)

(72) Inventors: Stephanie Anne Bare, Naples, FL (US); Christopher Kreulen, Sacramento, CA (US)

(73) Assignee: Arthrex, Inc., Naples, FL (US)

( * ) Notice: Subject to any disclaimer, the term of this patent is extended or adjusted under 35 U.S.C. 154(b) by 109 days.

This patent is subject to a terminal disclaimer.

(21) Appl. No.: 17/323,581

(22) Filed: May 18, 2021

(65) Prior Publication Data

US 2021/0267652 A1  Sep. 2, 2021

Related U.S. Application Data

(63) Continuation of application No. 14/874,893, filed on Oct. 5, 2015, now Pat. No. 11,020,157.

(51) Int. Cl.
*A61B 17/80* (2006.01)
*A61B 17/86* (2006.01)

(52) U.S. Cl.
CPC ...... *A61B 17/8014* (2013.01); *A61B 17/8057* (2013.01); *A61B 17/863* (2013.01); *A61B 17/8605* (2013.01)

(58) Field of Classification Search
CPC ............ A61B 17/8052; A61B 17/8057; A61B 17/8605; A61B 17/861; A61B 17/8615; A61B 17/863
See application file for complete search history.

(56) References Cited

U.S. PATENT DOCUMENTS

| | | | |
|---|---|---|---|
| 4,858,601 A | 8/1989 | Glisson | |
| 5,562,672 A | 10/1996 | Huebner et al. | |
| 5,601,553 A * | 2/1997 | Trebing | A61B 17/8605 |
| | | | 606/301 |
| 5,954,722 A * | 9/1999 | Bono | A61B 17/863 |
| | | | 606/281 |
| 6,030,162 A | 2/2000 | Huebner | |

(Continued)

FOREIGN PATENT DOCUMENTS

| | | |
|---|---|---|
| DE | 20 2011 100 537 U1 | 9/2011 |
| WO | 2009063489 A2 | 5/2009 |

(Continued)

OTHER PUBLICATIONS

International Search Report and Written Opinion of the International Searching Authority for International application No. PCT/US2016/045127 dated Oct. 11, 2016.

(Continued)

*Primary Examiner* — Anu Ramana
(74) *Attorney, Agent, or Firm* — Carlson, Gaskey & Olds, P.C.

(57) ABSTRACT

A surgical screw according to an exemplary aspect of the present disclosure includes, among other things, a shaft portion that extends between a proximal end and a distal end, the shaft portion including a first thread having a variable pitch and a head portion extending from the proximal end of the shaft portion. The head portion includes a second thread having a pitch that is equal to a pitch of at least a portion of the variable pitch.

21 Claims, 3 Drawing Sheets

(56) References Cited

U.S. PATENT DOCUMENTS

| | | |
|---|---|---|
| 6,193,721 B1 | 2/2001 | Michelson |
| 6,565,573 B1 * | 5/2003 | Ferrante ............... A61B 17/863 606/62 |
| 7,179,260 B2 | 2/2007 | Gerlach et al. |
| 7,537,596 B2 | 5/2009 | Jensen |
| 7,909,858 B2 | 3/2011 | Gerlach et al. |
| 8,187,309 B2 | 5/2012 | Castaneda et al. |
| 8,425,574 B2 | 4/2013 | Huebner et al. |
| 8,728,129 B2 | 5/2014 | Fritzinger et al. |
| 8,740,955 B2 | 6/2014 | Bottlang et al. |
| 8,790,376 B2 | 7/2014 | Fritzinger et al. |
| 2005/0010226 A1 | 1/2005 | Grady et al. |
| 2005/0192578 A1 | 9/2005 | Horst |
| 2006/0149265 A1 | 7/2006 | James et al. |
| 2009/0118773 A1 * | 5/2009 | James ............... A61B 17/8057 606/301 |
| 2011/0118795 A1 * | 5/2011 | Hashmi ............... A61B 17/863 606/315 |
| 2012/0029579 A1 | 2/2012 | Bottlang et al. |
| 2013/0150901 A1 | 6/2013 | Kortenbach et al. |
| 2014/0031879 A1 | 1/2014 | Sixto, Jr. et al. |
| 2014/0277190 A1 | 9/2014 | Splieth et al. |
| 2015/0209091 A1 | 7/2015 | Sixto, Jr. et al. |

FOREIGN PATENT DOCUMENTS

| | | |
|---|---|---|
| WO | 2014057405 A1 | 4/2014 |
| WO | 2015/100149 A1 | 7/2015 |

OTHER PUBLICATIONS

International Preliminary Report on Patentability. International Application No. PCT/US2016/045127, dated Dec. 20, 2017.

European Examination Report for European Patent Application No. 16751099.9, dated Oct. 17, 2019.

* cited by examiner

DETAIL A

DETAIL B

SURGICAL SCREW SYSTEM

CROSS-REFERENCE TO RELATED APPLICATIONS

This is a continuation of U.S. patent application Ser. No. 14/874,893 filed on Oct. 5, 2015, now U.S. Pat. No. 11,020,157 granted on Jun. 1, 2021.

BACKGROUND

This disclosure relates to a surgical screw system that includes a bone plate and a surgical screw.

SUMMARY

This disclosure details a surgical screw system. Such a surgical screw system can be used in the repair of fractured bones. The surgical screw system includes a bone plate and a surgical screw insertable into an opening of the bone plate. The surgical screw may both create compression across a fracture and engage an opening to lock the bone plate to a bone. Thereby, the surgical screw system is both a compression and locking system.

A surgical screw according to an exemplary aspect of the present disclosure includes, among other things, a shaft portion that extends between a proximal end and a distal end, the shaft portion including a first thread having a variable pitch and a head portion extending from the proximal end of the shaft portion. The head portion includes a second thread having a pitch that is equal to a pitch of at least a portion of the variable pitch.

In a further non-limiting embodiment of the foregoing surgical screw, the first thread extends along an entire length from the proximal end to the distal end.

In a further non-limiting embodiment of either of the foregoing surgical screws, the variable pitch decreases in a direction that extends from the distal end toward the proximal end.

In a further non-limiting embodiment of any of the foregoing surgical screws, the shaft portion tapers in a direction from the proximal end toward the distal end.

In a further non-limiting embodiment of any of the foregoing surgical screws, the head portion includes a first diameter that is greater than a second diameter of the shaft portion at the proximal end.

In a further non-limiting embodiment of any of the foregoing surgical screws, the first thread includes a first pitch along a first segment of the shaft portion and a second pitch that is different from the first pitch along a second segment of the shaft portion.

In a further non-limiting embodiment of any of the foregoing surgical screws, the first pitch is constant along the first segment and the second pitch is constant along the second segment.

In a further non-limiting embodiment of any of the foregoing surgical screws, the first pitch is nearer to the distal end and the second pitch is nearer to the proximal end, and the second pitch is smaller than the first pitch.

In a further non-limiting embodiment of any of the foregoing surgical screws, the pitch of the second thread is the same pitch as the pitch of the first thread at the proximal end of the shaft portion.

In a further non-limiting embodiment of any of the foregoing surgical screws, the variable pitch of the first thread incrementally changes along a length of the shaft portion.

In a further non-limiting embodiment of any of the foregoing surgical screws, the variable pitch of the first thread continuously changes along a length of the shaft portion.

A surgical screw system according to another exemplary aspect of the present disclosure includes, among other things, a bone plate including at least one opening and a surgical screw received in the at least one opening. The surgical screw includes a head portion configured to lock within the at least one opening and a shaft portion configured to create compression across a fractured bone. The shaft portion includes a first thread that includes a variable pitch.

In a further non-limiting embodiment of the foregoing system, the at least one opening is a threaded opening.

In a further non-limiting embodiment of either of the foregoing systems, a second thread of the head portion is configured to engage the threaded opening.

In a further non-limiting embodiment of any of the foregoing systems, the variable pitch of the first thread incrementally changes along a length of the shaft portion.

In a further non-limiting embodiment of any of the foregoing systems, the variable pitch of the first thread continuously changes along a length of the shaft portion.

In a further non-limiting embodiment of any of the foregoing systems, the variable pitch is a decreasing pitch that decreases in a direction that extends from a distal end of the shaft portion toward a proximal end of the shaft portion.

In a further non-limiting embodiment of any of the foregoing systems, the head portion includes a second thread, and the second thread includes a pitch that is the same pitch as at least a portion of the variable pitch.

In a further non-limiting embodiment of any of the foregoing systems, the second thread is separate from the first thread.

In a further non-limiting embodiment of any of the foregoing systems, the first thread includes a first pitch along a first segment of the shaft portion and a second pitch that is different from the first pitch along a second segment of the shaft portion.

In a further non-limiting embodiment of any of the foregoing systems, the first pitch is constant along the first segment and the second pitch is constant along the second segment, and the first pitch is nearer to a distal end of the shaft portion and the second pitch is nearer to a proximal end of the shaft portion, and the second pitch is smaller than the first pitch.

A surgical method according to another exemplary aspect of the present disclosure includes, among other things, positioning a bone plate against a fractured bone such that the bone plate is generally parallel to a fracture line of the fractured bone. A surgical screw is inserted through an opening of the bone plate such that the surgical screw extends across the fracture line between a first fragment and a second fragment of the fractured bone. During insertion of the surgical screw, compression is imparted across the fracture line to draw the first fragment and the second fragment closer together with a shaft portion of the surgical screw that includes a thread having a variable pitch. The method includes engaging the opening of the bone plate with a head portion of the surgical screw to substantially lock the bone plate to the fractured bone.

The embodiments, examples and alternatives of the preceding paragraphs, the claims, or the following description and drawings, including any of their various aspects or respective individual features, may be taken independently or in any combination. Features described in connection with one embodiment are applicable to all embodiments, unless such features are incompatible.

The various features and advantages of this disclosure will become apparent to those skilled in the art from the following detailed description. The drawings that accompany the detailed description can be briefly described as follows.

DETAILED DESCRIPTION

This disclosure describes a surgical screw system. The surgical screw system includes a bone plate and a surgical screw. The surgical screw system can be used in the repair of fractured bones. The bone plate can be fixated to a fractured bone using one or more surgical screws. In an embodiment, a single screw both locks a bone plate to a fractured bone and imparts compression across the fracture to draw the fractured surfaces of the bone together.

In some embodiments, a surgical screw includes a head portion configured to engage an opening of a bone plate and a shaft portion configured to create compression across a fracture line of a fractured bone. The shaft portion may include a thread having a variable pitch. The head portion may include a thread having a pitch that is the same pitch as at least a portion of the thread of the shaft portion. In an embodiment, the head portion of a surgical screw and the top of the shaft of the surgical screw have the same thread pitch while the entire length of the surgical screw shaft has a variable pitch.

Surgical methods comprise utilizing any embodiment of the surgical screw system disclosed herein. In an embodiment, a surgical method includes inserting a surgical screw through an opening of a bone plate, wherein the surgical screw extends across a fracture line between a first bone fragment and a second bone fragment of a fractured bone. In an embodiment, the surgical screw can be any of the surgical screws disclosed herein. In an embodiment, inserting a surgical screw imparts compression across the fracture line to draw the first fragment and the second fragment closer together with a shaft portion of the surgical screw. In an embodiment, a shaft portion of the surgical screw has a variable pitch. In a further embodiment, a surgical method includes engaging an opening of a bone plate with a head portion of a surgical screw as disclosed herein to substantially lock a bone plate to a fractured bone. In an embodiment, a surgical method includes positioning a bone plate against a fractured bone, wherein the bone plate is generally parallel to a fracture line of the fractured bone.

In an embodiment, a surgical method includes engaging a bone plate with a surgical screw against a fractured bone, wherein the fractured bone is compressed and the bone plate is locked to the fractured bone. In an embodiment of the surgical method, the surgical screw extends across a fracture line to engage a first bone fragment and a second bone fragment of the fractured bone.

These and other features are described in greater detail in the following paragraphs of this detailed description.

Figure 1:
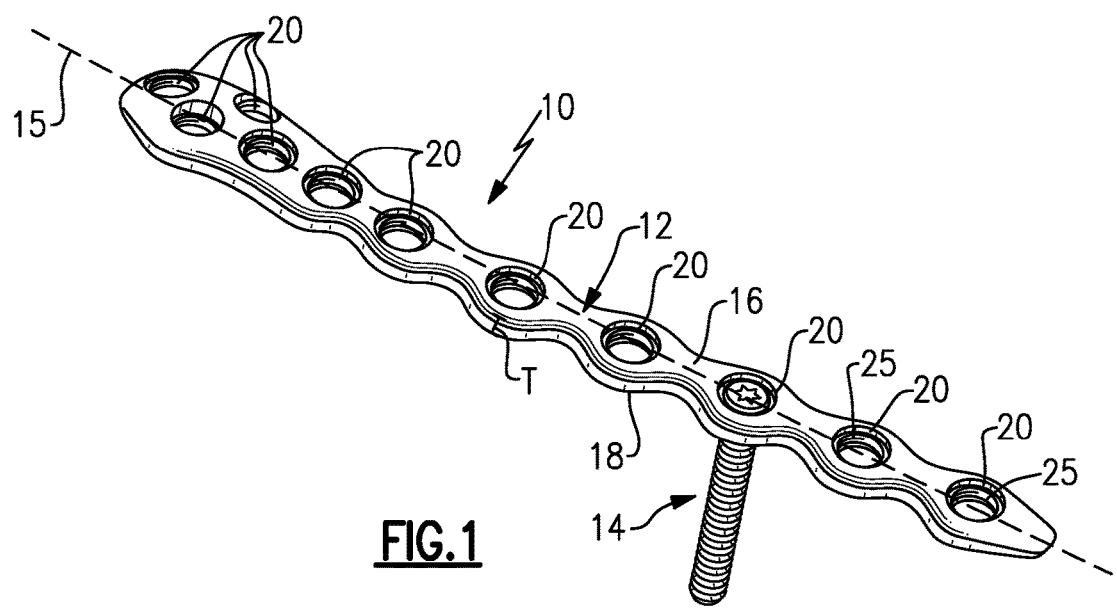
FIG. 1 illustrates a surgical screw system for repairing a fractured bone.

FIG. 1 illustrates a surgical screw system 10 for repairing a fractured bone. The surgical screw system 10 could be utilized to compress bone fragments of any fractured bone of the human musculoskeletal system. The surgical screw system 10 includes a bone plate 12 and one or more surgical screws 14 (only one shown in FIG. 1).

The bone plate 12 includes an exterior surface 16 and a bone contacting surface 18 that both extend along a longitudinal axis 15. A thickness T of the bone plate 12 extends between the exterior surface 16 and the bone contacting surface 18. The bone plate 12 may embody any size or shape. The size and shape of the bone plate 12 is not limited to the configuration shown in FIG. 1. The actual size and shape of the bone plate 12 depends on the anatomic location of the surgery being performed, among other criteria.

The bone plate 12 includes a plurality of openings 20. The openings 20 extend through the thickness T of the bone plate 12. For example, each opening 20 may extend from the exterior surface 16, across the thickness T, and through the bone contacting surface 18. At least a portion of the openings 20 may be threaded openings. For example, the openings 20 may include threads 25 that engage the surgical screws 14.

Each opening 20 is configured to receive one of the surgical screws 14. The bone plate 12 could include any number of openings 20, and is not limited to the specific number of openings 20 shown in FIG. 1. The bone plate 12 may be made of a metallic material, a plastic material, a carbon fiber, or any other suitable material.

The bone plate 12 may accommodate one or more surgical screws 14. Each surgical screw 14 is configured to both lock within the opening 20 of the bone plate 12 and impart compression across a fracture line between bone fragments of a fractured bone to draw the bone fragments together. In other words, the surgical screws 14 of this disclosure embody a hybrid design that can function as both a locking screw and a compression screw in a single screw design.

Figure 2:
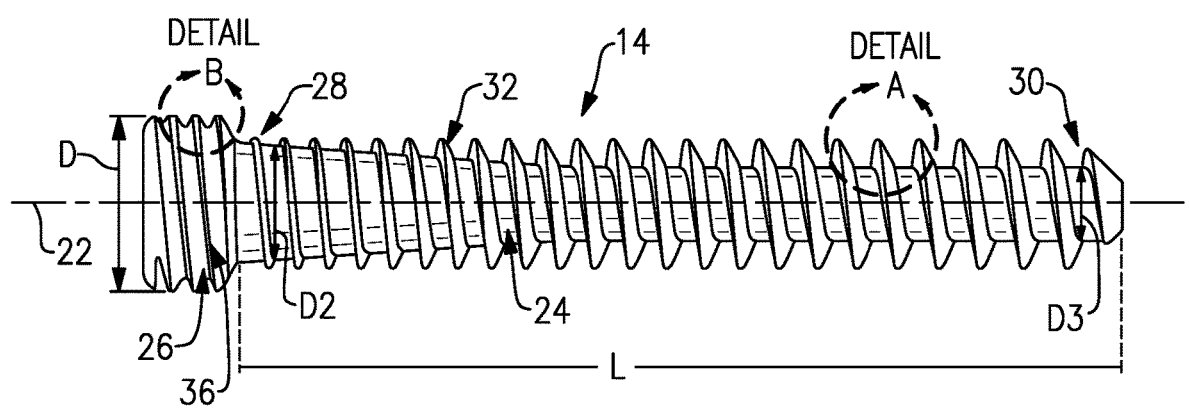
FIG. 2 illustrates a surgical screw of a surgical screw system.

FIG. 2 illustrates the surgical screw 14 of the surgical screw system 10 shown in FIG. 1. The surgical screw 14 may embody any size or shape. The actual size and shape of the surgical screw 14 may depend on the anatomic location of the surgery being performed, among other criteria.

The surgical screw 14 may be made of any biocompatible material, including but not limited to, metallic materials, plastic materials, etc. The surgical screw 14 may also embody either a solid design or, optionally, a cannulated design. A cannulated design enables the surgical screw 14 to be placed over a guidewire to aid surgical insertion into a bone.

The surgical screw 14 extends along a longitudinal axis 22 and includes a shaft portion 24 and a head portion 26. The shaft portion 24 extends between a proximal end 28, which is located near the head portion 26, and a distal end 30, which is spaced further from the head portion 26 than the proximal end 28. The head portion 26 may extend from the proximal end 28 of the shaft portion 24.

In one non-limiting embodiment, the head portion 26 includes a diameter D1 that is larger than a diameter D2 of the proximal end 28 of the shaft portion 24. In another non-limiting embodiment, the shaft portion 24 of the surgical screw 14 tapers between the proximal end 28 and the distal end 30. Accordingly, the distal end 30 of the shaft portion 24 may include a diameter D3 that is smaller than the diameter D2 of the proximal end 28 and smaller than the diameter D1 of the head portion 26.

The shaft portion 24 includes a thread 32 that extends along at least a portion of the length L of the shaft portion 24. In one non-limiting embodiment, the thread 32 spirals around the shaft portion 24 and spans across the entire length L of the shaft portion 24 between the proximal end 28 and the distal end 30. The shaft portion 24 could optionally include areas along the length L that are non-threaded.

The thread 32 may include a variable pitch. The variable pitch is a thread pitch that changes along the length L of the thread 32. In one non-limiting embodiment, the pitch of the thread 32 incrementally changes at predefined segments of the length L. For example, in one non-limiting embodiment, the pitch of the thread 32 changes every 0.01 inches (0.254 mm) of the thread 32. However, the variable pitch could incrementally change at other predefined segments. In one non-limiting embodiment, the pitch of the thread 32 incrementally changes along the entire length L of the thread 32. In another non-limiting embodiment, the pitch of the thread 32 incrementally changes along only a portion of the length L of the thread 32 but not along the entire length L of the thread 32.

In a non-limiting embodiment, the pitch of the thread 32 changes continuously along the length L of the thread 32.

Figure 3:
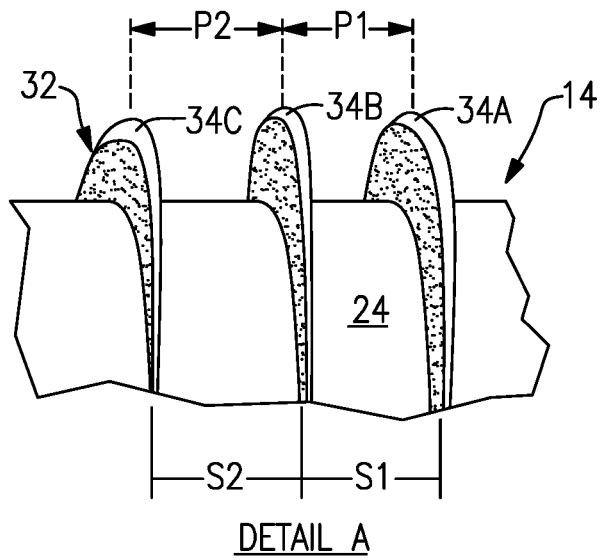
FIG. 3 is an enlarged view of Detail A of FIG. 2.

In an embodiment, the variable pitch of the thread 32 of the surgical screw 14 is further illustrated in FIG. 3, which depicts Detail A of FIG. 2. The thread 32 may include a first pitch P1 along a first segment S1 of the shaft portion 24 and may include a second pitch P2 that is different from the first pitch P1 along a second segment S2 of the shaft portion 24. The first pitch P1 is the distance from one crest 34A of the thread 32 to a corresponding point of an adjacent crest 34B in the first segment S1, and the second pitch P2 is the distance from the crest 34B to a corresponding point of an adjacent crest 34C of the thread 32 within the second segment S2. The pitch of the thread 32 is constant within each of segments S1, S2 but incrementally changes to a different pitch as the thread 32 transitions from the first segment S1 to the second segment S2.

The first pitch P1, which is closer to the distal end 30, may be a larger pitch than the second pitch P2, which is located further toward the proximal end 28 of the surgical screw 14. In other words, the variable pitch of the thread 32 includes a decreasing pitch that decreases in a direction from the distal end 30 toward the proximal end 28. The decreasing pitch could continue across multiple segments along the entire length L of the shaft portion 24. In this manner, the portion of the thread 32 nearer to the distal end 30 of the shaft portion 24 cuts a path into bone faster than the portion of the thread 32 nearer to the proximal end 28. The variable pitch of the thread 32 therefore tends to create compression across a fracture line during insertion in a manner that draws bone fragments together to promote healing of the fractured bone.

Figure 4:
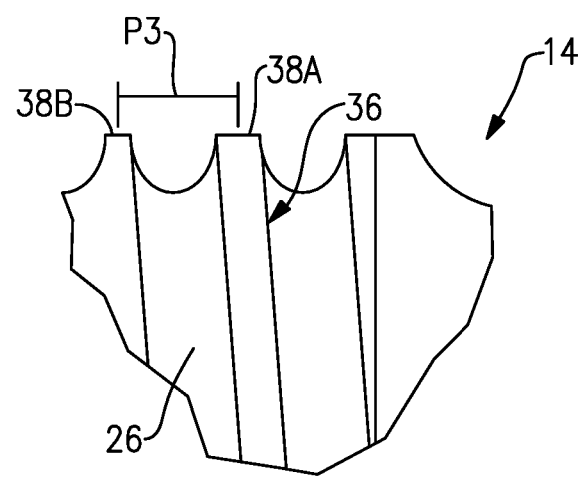
FIG. 4 is an enlarged view of Detail B of FIG. 2.

Referring now to FIGS. 2 and 4, the head portion 26 may also include a thread 36. In one non-limiting embodiment, the thread 36 is separate from the thread 32 of the shaft portion 24. In another non-limiting embodiment, the thread 36 is an extension of the thread 32 of the shaft portion 24. The thread 36 of the head portion 26 may include a third pitch P3 (see FIG. 4). The third pitch P3 is the distance from one crest 38A of the thread 36 to a corresponding point of an adjacent crest 38B of the thread 36. In one non-limiting embodiment, the third pitch P3 of the thread 36 is constant over the entire head portion 26.

The third pitch P3 may be a different pitch from the pitch of any portion of the thread 32, or could be the same pitch as the pitch of any of the segments of the thread 32. In one non-limiting embodiment, the third pitch P3 is the same pitch as the pitch of the thread 32 at the proximal end 28 of the shaft portion 24.

Figure 5:
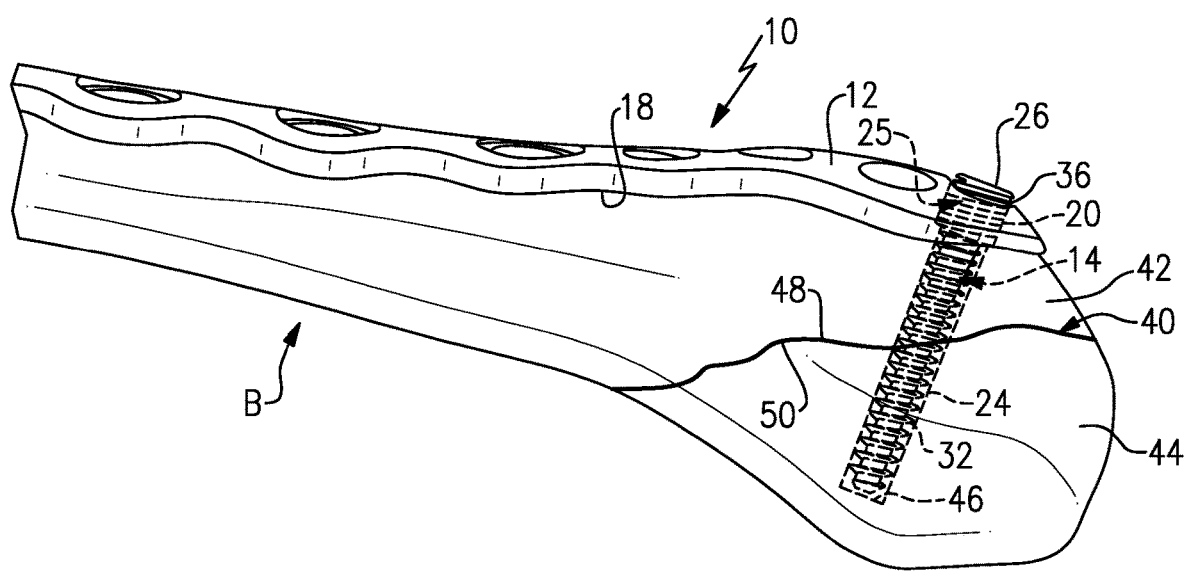
FIG. 5 schematically illustrates the use of a surgical screw system to repair a fractured bone.

FIG. 5 schematically illustrates use of the surgical screw system 10 to repair a fractured bone B. In one non-limiting embodiment, the fractured bone B is a fractured distal tibia. However, this disclosure is not limited to distal tibia repairs, and the surgical screw system 10 could be configured to repair any fractured bone.

The fractured bone B illustrated in FIG. 5 includes a fracture line 40 that separates a first bone fragment 42 and a second bone fragment 44 of the fractured bone B. The first bone fragment 42 and the second bone fragment 44 can be completely or partially separated from one another by the fracture line 40.

The bone plate 12 is positioned against an exterior surface of one of the bone fragments, here the first bone fragment 42. The bone plate 12 may be positioned such that its bone contacting surface 18 is received against the first bone fragment 42. The bone plate 12 can be configured to generally match the contour of the bone being repaired. In one non-limiting embodiment, the bone plate 12 is positioned such that it extends along a path that is generally parallel to the fracture line 40 of the fractured bone B.

The surgical screw 14 may be inserted through one of the openings 20 of the bone plate 12. A pilot hole 46 may optionally be drilled into the fractured bone B before inserting the surgical screw 14. During insertion, the thread 32 of the shaft portion 24 of surgical screw 14 cuts a path into the fractured bone B. Because of the variable pitch of the thread 32, which decreases along the length of the shaft portion 24, each successive turn of the thread 32 exerts pressure against the upper portion of the path cut by the thread 32, thereby tending to compress the bone fragments 42, 44 along the length of the shaft portion 24 of the surgical screw 14. By the time the surgical screw 14 is fully installed across the fracture line 40, the trailing portions of the thread 32 compress bone as these portions cut further into the path formed by the leading portions of the thread 32. This compression has the tendency to draw the bone fragments 42, 44 together along surfaces 48, 50, respectively, thereby promoting healing of the fractured bone B.

Once fully inserted, the head portion 26 of the surgical screw 14 can engage the opening 20 of the bone plate 12. For example, the thread 36 of the head portion 26 may engage threads 25 of the opening 20. This engagement substantially locks the surgical screw 14 to the bone plate 12 and therefore stabilizes the bone plate 12 relative to the fractured bone B.

The surgical screws of this disclosure provide a hybrid screw design that achieves the functions of both compression screws and locking screws within a single screw design. The exemplary surgical screws therefore allow for unicortical fixation and compression between bone fragments.

Although the different non-limiting embodiments are illustrated as having specific components, the embodiments of this disclosure are not limited to those particular combinations. It is possible to use some of the components or features from any of the non-limiting embodiments in combination with features or components from any of the other non-limiting embodiments.

It should be understood that like reference numerals identify corresponding or similar elements throughout the several drawings. It should also be understood that although a particular component arrangement is disclosed and illustrated in these exemplary embodiments, other arrangements could also benefit from the teachings of this disclosure.

The foregoing description shall be interpreted as illustrative and not in any limiting sense. A worker of ordinary skill in the art would understand that certain modifications could come within the scope of this disclosure. For these reasons, the following claims should be studied to determine the true scope and content of this disclosure.

What is claimed is:

1. A surgical method, comprising:
positioning a bone plate against a fractured bone including a first bone fragment and a second bone fragment;
drilling a pilot hole in the fractured bone;
inserting a surgical screw through an opening of the bone plate such that the surgical screw extends across a fracture line between the first bone fragment and the second bone fragment and through the second bone fragment of the fractured bone, wherein a shaft portion of the surgical screw comprises:
a) a longitudinal axis,
b) a shaft thread having a minor diameter and a shaft pitch, wherein the shaft thread comprises a proximal portion having a proximal pitch and a distal portion having a distal pitch,
c) a proximal region including the proximal portion of the shaft thread and a proximal end, and
d) a distal region including the distal portion of the shaft thread and a distal end, wherein the shaft thread extends along an entire length of the shaft portion from the proximal end to the distal end, and the distal pitch of the distal thread is larger than the proximal pitch of the proximal thread, and
e) a head portion including a head thread that is an extension of the shaft thread of the shaft portion, wherein a head pitch of the head thread of the head portion has the same pitch as the proximal pitch of the shaft thread at the proximal end of the shaft portion, and a diameter of the head portion is greater than a greatest diameter of the shaft portion,
wherein the minor diameter of the shaft thread of the shaft portion decreases in a direction towards the longitudinal axis of the shaft portion from the proximal end of the shaft portion to a position intermediate the proximal end and the distal end of the shaft portion such that the shaft portion tapers inwardly towards the longitudinal axis of the shaft portion, and the taper terminates intermediate the proximal end and the distal end of the shaft portion;
cutting a path through the pilot hole into the fractured bone with the surgical screw;
moving the distal region of the shaft portion through the second bone fragment to provide compression between the first bone fragment and the second bone fragment;
engaging the opening of the bone plate with the head thread of the head portion of the surgical screw to substantially lock the bone plate to the fractured bone to stabilize the bone plate relative to the fractured bone; and
locking the head thread of the head portion in the threaded opening of the bone plate.

2. The surgical method as recited in claim 1, wherein the shaft thread has a variable pitch comprised of multiple segments each having a different pitch, the multiple segments comprise a first segment having a first pitch and a second segment having a second pitch, the first pitch is constant along the first segment, the second pitch is constant along the second segment, and the variable pitch decreases incrementally from the distal end to the proximal end.

3. The surgical method as recited in claim 1, wherein the shaft pitch of the shaft portion decreases from the distal end to the proximal end.

4. The surgical method as recited in claim 1 wherein a proximal portion of the shaft portion located proximate to the head portion tapers distally in a direction from the proximal end to the distal end of the shaft portion.

5. A surgical method, comprising:
inserting a surgical screw through an opening of a bone plate such that the surgical screw extends across a fracture line between a first bone fragment and a second bone fragment of a fractured bone, wherein the surgical screw includes a shaft portion and a head portion,
wherein the shaft portion comprises:
a) a longitudinal axis,
b) a shaft thread having a minor diameter and a shaft pitch, wherein the shaft thread comprises a proximal portion having a proximal pitch and a distal portion having a distal pitch,
c) a proximal region including the proximal portion of the shaft thread and a proximal end, and
d) a distal region including the distal portion of the shaft thread and a distal end, wherein the distal pitch of the distal thread is larger than the proximal pitch of the proximal thread,
wherein the head portion comprises a head thread that is an extension of the shaft thread of the shaft portion, and a diameter of the head portion is greater than a greatest diameter of the shaft portion,
wherein the minor diameter of the shaft thread of the shaft portion decreases in a direction towards the longitudinal axis of the shaft portion from the proximal end of the shaft portion to a position intermediate the proximal end and the distal end of the shaft portion such that the shaft portion tapers inwardly towards the longitudinal axis of the shaft portion, and the taper terminates intermediate the proximal end and the distal end of the shaft portion; and
moving the distal region of the shaft portion through the second bone fragment to provide compression between the first bone fragment and the second bone fragment.

6. The surgical method as recited in claim 5, including positioning the bone plate against the fractured bone.

7. The surgical method as recited in claim 5, including engaging the opening of the bone plate with the head thread of the head portion of the surgical screw to substantially lock the bone plate to the fractured bone to stabilize the bone plate relative to the fractured bone.

8. The surgical method as recited in claim 5, wherein a head pitch of the head thread of the head portion has the same pitch as the proximal pitch of the shaft thread at the proximal end of the shaft portion.

9. The surgical method as recited in claim 5, wherein the opening of the bone plate comprises a threaded opening, the method including locking the head thread of the head portion in the threaded opening of the bone plate.

10. The surgical method as recited in claim 5, including drilling a pilot hole in the fractured bone prior to inserting the surgical screw through the opening of the bone plate and then cutting a path through the pilot hole into the fractured bone with the surgical screw.

11. The surgical method as recited in claim 5, wherein the shaft thread extends along an entire length of the shaft portion from the proximal end to the distal end.

12. The surgical method as recited in claim 5, wherein the shaft pitch of the shaft portion decreases from the distal end to the proximal end.

13. The surgical method as recited in claim 5, wherein the shaft thread has a variable pitch comprised of multiple segments each having a different pitch, the multiple segments comprise a first segment having a first pitch and a second segment having a second pitch, the first pitch is constant along the first segment, the second pitch is constant along the second segment, and the variable pitch decreases incrementally from the distal end to the proximal end.

14. The surgical method as recited in claim 5 wherein a proximal portion of the shaft portion located proximate to the head portion tapers distally in a direction from the proximal end to the distal end of the shaft portion.

15. A surgical method, comprising:
inserting a surgical screw through an opening of a bone plate such that the surgical screw extends between a first bone and a second bone, wherein surgical screw includes a shaft portion and a head portion,
wherein the shaft portion comprises:
a) a longitudinal axis,
b) a shaft thread having a minor diameter and a shaft pitch, wherein the shaft thread comprises a proximal portion having a proximal pitch and a distal portion having a distal pitch,
c) a proximal region including the proximal portion of the shaft thread and a proximal end, and
d) a distal region including the distal portion of the shaft thread and a distal end, wherein the distal pitch of the distal thread is larger than the proximal pitch of the proximal thread,
wherein the head portion comprises a head thread that is an extension of the shaft thread of the shaft portion, and a diameter of the head portion is greater than a greatest diameter of the shaft portion,
wherein the minor diameter of the shaft thread of the shaft portion decreases in a direction towards the longitudinal axis of the shaft portion from the proximal end of the shaft portion to a position intermediate the proximal end and the distal end of the shaft portion such that the shaft portion tapers inwardly towards the longitudinal axis of the shaft portion, and the taper terminates intermediate the proximal end and the distal end of the shaft portion; and
moving the distal region of the shaft portion through the second bone to provide compression between the first bone and the second bone.

16. The surgical method as recited in claim 15, including engaging the opening of the bone plate with the head thread of the head portion of the surgical screw to substantially lock the bone plate to the first bone and the second bone to stabilize the bone plate relative to the first bone and the second bone, wherein head pitch of the head thread of the head portion has the same pitch as the proximal pitch of the shaft thread at the proximal end of the shaft portion, and the opening of the bone plate comprises a threaded opening, the method including locking the head thread of the head portion in the threaded opening of the bone plate.

17. The surgical method as recited in claim 15, including drilling a pilot hole in the first bone and the second bone prior to inserting the surgical screw through the opening of the bone plate and then cutting a path through the pilot hole into the first bone and the second bone with the surgical screw.

18. The surgical method as recited in claim 15, wherein the shaft thread extends along an entire length of the shaft portion from the proximal end to the distal end.

19. The surgical method as recited in claim 15, wherein the shaft pitch of the shaft portion decreases from the distal end to the proximal end.

20. The surgical method as recited in claim 15, wherein the shaft thread has a variable pitch comprised of multiple segments each having a different pitch, the multiple segments comprise a first segment having a first pitch and a second segment having a second pitch, the first pitch is constant along the first segment, the second pitch is constant along the second segment, and the variable pitch decreases incrementally from the distal end to the proximal end.

21. The surgical method as recited in claim 15 wherein a proximal portion of the shaft portion located proximate to the head portion tapers distally in a direction from the proximal end to the distal end of the shaft portion.

* * * * *